United States Patent [19]
Hartwig et al.

[11] Patent Number: 6,100,398
[45] Date of Patent: *Aug. 8, 2000

[54] TRANSITION METAL-CATALYZED PROCESS FOR PREPARING N-ARYL AMINE COMPOUNDS

[75] Inventors: John F. Hartwig; Motoi Kawatsura, both of New Haven; Sheila I. Hauck, West Haven; Kevin H. Shaughnessy; Luis M. Alcazar-Roman, both of New Haven, all of Conn.

[73] Assignee: Yale University, New Haven, Conn.

[ * ] Notice: This patent is subject to a terminal disclaimer.

[21] Appl. No.: 09/343,383

[22] Filed: Jun. 30, 1999

Related U.S. Application Data

[63] Continuation-in-part of application No. 09/172,497, Oct. 14, 1998, Pat. No. 5,977,361
[60] Provisional application No. 60/062,211, Oct. 16, 1997.
[51] Int. Cl.$^7$ .......................... C07C 209/10; C07C 473/00
[52] U.S. Cl. ...................... 544/264; 548/400; 548/300.1; 548/469; 548/360.1; 548/440; 548/356.1; 564/386; 564/395; 564/405; 560/24; 558/418
[58] Field of Search .......................... 558/418; 544/264; 548/400, 300.1, 469, 360.1, 440, 356.1; 564/386, 395, 405

[56] References Cited

U.S. PATENT DOCUMENTS

| | | | |
|---|---|---|---|
| 5,576,460 | 11/1996 | Buchwald et al. | 564/386 |
| 5,847,166 | 12/1998 | Buchwald et al. | 549/355 |
| 5,977,361 | 11/1999 | Hartwig et al. | 544/264 |

OTHER PUBLICATIONS

Barton, et al. "Metallic Copper Catalysts Of N–Arylation of Amines By Triarylbismuth Diacylates", *Tetrahedron Letters*, 27, No. 31, 3615–3618 (1986).

Lopez–Alvarado, et al "New Synthetic Application of Aryl-lead Triacetates. N–Arylation of Azoles", *J. Org. Chem.*, 60: 5678–5682 (1995).

Khan, et al. "Synthesis of Heterocyclic Compounds. Part II. N–Arylazoles by Ullmann Condensation", *J. Chem. Soc.*, 85–91 (1970).

Lam, et al., "New Aryl/Heteroaryl C–N Bond Cross–coupling Reactions via Arylboronic Acid/Cupric Acetate Arylation", *Tetrahedron Letters*, 39: 2941–2944 (1998).

Beletskaya, et al., "Pd–and Cu–catalyzed selective Arylation of Benzotriazole by Diaryliodonium salts in Water", *Tetrahedron Letters*, 39: 5621–5622 (1998).

Smith, et al., "A Novel and Selective Method for the N–Arylation of Indoles Mediated by KF/AL$_2$O$_3$", *Tetrahedron Letters*, 37, No. 3, 299–302 (1996).

Nishiyama, "Synthesis of N–Arylpiperazines from Aryl Halides and Piperazine under a Palladium Tri–ter–butylphosphine Catalyst", *Tetrahedron Letters*, 39: 617 (1998).

Hamann, et al., "Sterically Hindered Chelating Alkyl Phosphines Provide Large Rate Acceleration in Palladium–Catalyzed Amination of Aryl Iodides, Bromides, and Chlorides, and the First Amination of Aryl Tosylates", *J. Amer. Chem. Soc.*, 120: 7369 (1998).

Yamamoto, "Palladium–Catalyzed Synthesis of Triarylamines from Aryl Halides and Diarylamines", *Tetrahedron Letters*, 39: 2367 (1998).

Old, et al., "A Highly Active Catalyst for Palladium–Catalyzed Cross–Coupling Reactions: Room–Temperature Suzuki Couplings and Amination of Unactivated Aryl Chlorides", *J. Amer. Chem. Soc.*, 120: 9722–9723 (1998).

Chan, "Promotion of Reaction of N–H Bonds with Triarylbismuth and Cupric Acetate", *Tetrahedron Letters*, 37:No. 50, pp. 9013–9016, (1996).

Holden, et al., "Iron–Mediated Synthesis of t–Butyl–N–(Aryloxy)Carbamates", *Synthetic Communications* 22: No. 17, pp. 2579–2586 (1992).

*Primary Examiner*—Richard L. Raymond
*Assistant Examiner*—Pavanaram K Gripada
*Attorney, Agent, or Firm*—Todd E. Garabedian; Wiggin & Dana

[57] ABSTRACT

Disclosed is a process for the preparation of N-aryl amine compounds, comprising reacting an amine compound with an arylating compound in the presence of a base and a transition metal catalyst under reaction conditions effective to form an N-aryl amine compound, the transition metal catalyst comprising a Group 8 metal and P(t-Bu)$_3$ as a ligand, and wherein the ratio of the ligand to the Group 8 metal is in the range of about 3:1 to about 0.25:1, and wherein the reaction temperature is less than 100° C. The process of the present invention provides a useful general method of N-arylation for the manufacture of pharmaceuticals, polymers, and the like.

26 Claims, No Drawings

TRANSITION METAL-CATALYZED PROCESS FOR PREPARING N-ARYL AMINE COMPOUNDS

CROSS-REFERENCE TO RELATED APPLICATIONS

This application is a Continuation-in-Part of application Ser. No. 09/172,497 filed Oct. 14, 1998 now U.S. Pat. No. 5,977,361, which claims the benefit of U.S. Provisional Application No. 60/062,211 filed Oct. 16, 1997.

STATEMENT OF GOVERNMENT SUPPORT

This application was made with United States Government support under Award Number 1-R29-GM382-01 from the National Institutes of Health. The U.S. Government has certain rights in this invention.

BACKGROUND OF THE INVENTION

1. Field of the Invention

This invention relates to a general process for producing N-arylated amine compounds, and more particularly to a general process for the formation of N-arylated amine compounds from amines and an arylating compound using transition metal catalysts containing $P(t-Bu)_3$ as a ligand.

2. Brief Description of the Related Art

N-Aryl amines are important substructures in natural products and industrial chemicals, such as pharmaceuticals, dyes, and agricultural products. The palladium-catalyzed amination of aryl halides has become an important method for the synthesis of arylamines found in pharmaceuticals, materials with important electronic properties, and ligands for early metal catalysts. Because of the importance of this synthetic method, approaches that provide high turnover numbers, fast reaction rates, high functional group compatibility, and increased scope of the aromatic C—N bond formation are highly desired.

It would be advantageous to prepare N-aryl compounds from arylating compounds such as aryl halides and/or aryl sulfonates because aryl halides are generally inexpensive and readily available, while aryl sulfonates are easily prepared from phenols. However, to date, methods of producing many types of N-aryl compounds are inefficient or economically unattractive.

In one example, workers at Tosoh Company reported that the catalysts containing the $P(t-Bu)_3$ ligand provided high turnover numbers for the formation of aryl piperazines with excess ligand (4:1 ratio of $P(t-Bu)_3$ ligand to Pd) at 120° C. (Nishiyama, N. et al., Tetrahedron Lett. 39:617–620 (1998); Yamamoto, T. et al., Tetrahedron Lett. 39:2367–2370 (1998)). However, the high temperatures of this reaction scheme make it unattractive for commercial use.

In another example, Hartwig et al. have shown that a sterically hindered alkylphosphine prepared in one step allows for room temperature amination of aryl halides and that another commercially available, sterically hindered alkylphosphine allows for the reaction of aryl chlorides with primary alkylamines under mild conditions (Hamann, B. C. and Hartwig, J. F., J. Am. Chem. Soc. 120:7369–7370 (1998)). It has also been reported recently that a P,N ligand containing a biphenyl backbone, which is prepared in three steps, generates a catalyst that leads to examples of room temperature amination chemistry with aryl bromides and room temperature Suzuki chemistry with aryl chlorides (Old, D. W. et al. J. Am. Chem. Soc. 120:9722–9723 (1998)). However, the multistep nature of the synthesis of this ligand makes it less attractive for commercial purposes.

In view of the above, a need exists for a general and efficient process of synthesizing N-aryl compounds from readily available arylating compounds and commercially available catalysts. The discovery and implementation of such a method would simplify the preparation of commercially significant organic N-aryl amine compounds and would enhance the development of novel polymers and pharmacologically active compounds. The present invention is believed to be an answer to that need.

SUMMARY OF THE INVENTION

In one aspect, the present invention is directed to a process for the preparation of N-aryl amine compounds, comprising reacting an amine compound with an arylating compound in the presence of a base and a transition metal catalyst under reaction conditions effective to form an N-aryl amine compound, the transition metal catalyst comprising a Group 8 metal and $P(t-Bu)_3$ as a ligand, and wherein the ratio of the ligand to the Group 8 metal is in the range of about 3:1 to about 0.25:1, and wherein the reaction temperature is less than 100° C.

In another aspect, the present invention is directed to a process for the preparation of N-aryl amine compounds, comprising reacting an amine compound selected from the group consisting of aryl amines, cyclic amines, secondary alkylamines, carbamates, and combinations thereof, and an arylating compound in the presence of a base and a transition metal catalyst comprising a Group 8 metal and $P(t-BU)_3$ as a ligand under reaction conditions effective to form an N-aryl amine compound, and wherein the ratio of the ligand to the Group 8 metal is in the range of about 3:1 to about 0.25:1, and wherein the reaction temperature is less than 100° C.

These and other aspects will become apparent upon reading the following detailed description of the invention.

DETAILED DESCRIPTION OF THE INVENTION

It now has been surprisingly found, in accordance with the present invention, that a solution is provided to the problem of providing a general and efficient process of synthesizing N-aryl amine compounds from an amine starting material, and an arylating compound. The present inventors have solved this problem by utilizing reaction conditions that include a base and a transition metal catalyst having a Group 8 metal in combination with the commercially available compound $P(t-Bu)_3$ as a ligand. In particular, the method of the present invention provides conditions and catalysts for the reaction of aryl halides with arylamines and with secondary alkylamines at room temperature using commercially available $P(t-Bu)_3$. The method of the present invention further provides conditions and catalysts for the reaction of aryl halides with arylamines or secondary alkylamines at approximately 70° C., and for improved arylation of indoles. The method of the present invention further provides conditions and catalysts for the arylation of carbamates, a reaction heretofore not available economically with present methodology and catalysts (Chan, D. M. T., Tetrahedron Lett. 37:9013–9016 (1996); Holden, M. S. et al., Synth. Comm. 2:2579–2586 (1992)). The method of the present invention provides a general process for production of a variety of N-aryl amine compounds, classes of compounds which are particularly significant in the development of pharmacologically active compounds and processing of polymers and oligomers.

The term "aryl" is defined herein as a compound whose molecules have the ring structure characteristic of benzene, naphthalene, phenanthroline, anthracene, heterocyclic, and the like. "Arylating compound" is defined as a compound which provides an aryl substituent in an organic reaction. "N-Aryl amine compounds" are those compounds in which a nitrogen atom of the compound is substituted with an aryl group. "Ph" as defined herein is understood to represent a phenyl group.

The process of the present invention is directed to the synthesis of N-aryl amine compounds. The process of the invention comprises reacting an amine-containing compound, such as an aryl amine, heterocyclic amine, secondary alkylamine, or carbamate, with an arylating compound in the presence of a base and a transition metal catalyst under reaction conditions effective to form an N-aryl amine compound. The transition metal catalyst comprises a Group 8 metal and P(t-Bu)$_3$ as a ligand. The general reaction is shown in Equation I.

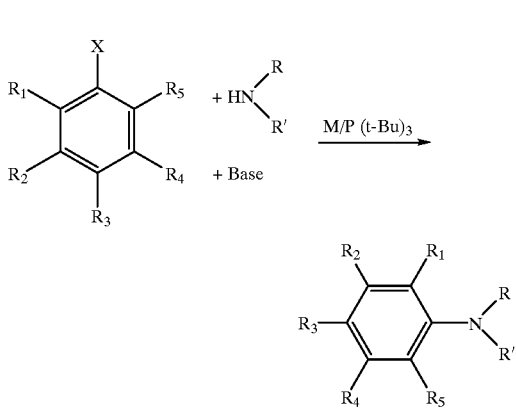

Briefly, in Scheme I, an arylating compound is reacted with an amine compound in the presence of a base, P(t-Bu)$_3$ as a ligand, and a Group 8 metal (M) to form an N-aryl amine compound. Each of these reactions and their components are described in more detail below.

The arylating compound used in the process of the present invention may be any arylating compound of the formula (II):

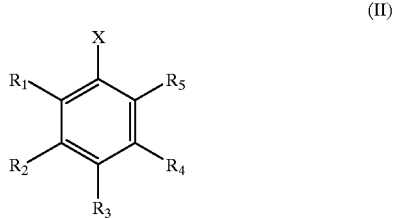

In formula II, X may be any halide atom (F, Cl, Br, I), or any sulfur-containing leaving group (e.g., triflate, sulfonate, tosylate, and the like) known in the art. Chlorides and bromides are especially preferred in the process of the present invention. $R_1$, $R_2$, $R_3$, $R_4$, and $R_5$ are independently selected from H; CN; alkyl, such as methyl, ethyl, propyl, n-butyl, t-butyl, and the like; alkoxy, vinyl, alkenyl, formyl; CF$_3$; CCl$_3$; halide, C$_6$H$_5$; amide such as C(O)N(CH$_3$)$_2$, C(O)N(CH$_2$CH$_3$)$_2$, C(O)N(CH$_2$CH$_2$CH$_3$)$_2$, and the like; acyl, such as C(O)—C$_6$H$_5$, and the like; ester, amino, thioalkoxy, phosphino, and the like. Arylating compound may also be a heterocyclic aromatic compound such as an azole or azole derivative, aryl phosphates, aryl trifluoroacetates, and the like. Alternatively, the arylating compound may be any aromatic or heteroaromatic halide, such as an aromatic or heteroaromatic chloride or bromide.

Preferred arylating compounds used in the process of the invention include aryl bromides and aryl chlorides. Examples of suitable aryl bromides include bromobenzene, 4-bromo-benzonitrile, 4-bromo-t-butyl benzene, 3-bromo-methoxy benzene, 2-bromo toluene, p-formyl phenyl bromide, p-CF$_3$ phenyl bromide, p-phenyl phenyl bromide, p-C(O)N(CH$_2$CH$_3$)$_2$ phenyl bromide, and p-C(O)—C$_6$H$_5$ phenyl bromide. Examples of suitable aryl chlorides include chlorobenzene, 4-chloro-benzonitrile, 4-chloro-t-butyl benzene, 3-chloro-methoxy benzene, 2-chloro toluene, p-formyl phenyl chloride, p-CF$_3$ phenyl chloride, p-phenyl phenyl chloride, p-C(O)N(CH$_2$CH$_3$)$_2$ phenyl chloride, and p-C(O)—C$_6$H$_5$ phenyl chloride.

According to the method of the invention, amine compounds include secondary amine compounds (e.g., R and R' are not H), aryl amines, cyclic or heterocyclic amines, and carbamates. Examples of useful secondary amines include dibutylamine (NHBu$_2$), dipropylamine (NHPr$_2$), diphenylamine (NHPh$_2$), and the like. Examples of cyclic amines include morphiline (C$_4$H$_9$NO), piperidine (C$_5$H$_{11}$N), azoles such as pyrrole, indole, and the like. Examples of useful carbamates include t-butylcarbamate (H$_2$NCOO-tBu).

The base shown in Scheme I is required for the process of the invention. Any base may be used so long as the process of the invention proceeds to the N-aryl amine product. It may be important in this regard that the base does not displace all of the chelating ligands on the catalyst. Nuclear magnetic resonance, infrared, and Raman spectroscopies, for example, are useful in determining whether the ligands remain bonded to the Group 8 metal, whether the ligands have been displaced by the base, or whether ligands have been displaced by reaction products.

Non-limiting examples of suitable bases include alkali metal hydroxides, such as sodium and potassium hydroxides; alkali metal alkoxides, such as sodium t-butoxide; metal carbonates, such as potassium carbonate, cesium carbonate, and magnesium carbonate; phosphates, such as potassium phosphate; alkali metal aryl oxides, such as potassium phenoxide or sodium phenoxide; alkali metal amides, such as lithium amide; tertiary amines, such as triethylamine and tributylamine; (hydrocarbyl)ammonium hydroxides, such as benzyltrimethyl-ammonium hydroxide and tetraethylammonium hydroxide; and diaza organic bases, such as 1,8-diazabicyclo[5.4.0]-undec-7-ene and 1,8-diazabicyclo-[2.2.2.]-octane. Preferably, the base is an alkali hydroxide or alkali alkoxide, more preferably, an alkali alkoxide, and most preferably, an alkali metal C$_{1-10}$ alkoxide.

The quantity of base which is used can be any quantity which allows for the formation of the N-aryl amine product. Preferably, the molar ratio of base to arylating compound ranges from about 1:1 to about 3:1, and more preferably between about 1:1 and 2:1.

The catalyst, designated M/P(t-Bu)$_3$ in Equation I, is characterized as comprising a metal atom or ion (M) and at least one or more ligands of P(t-Bu)$_3$. The metal atom or ion is required to be a Group 8 transition metal, that is, a metal selected from iron, cobalt, nickel, ruthenium, rhodium, palladium, osmium, iridium, and platinum. More preferably, the Group 8 metal is palladium, platinum, or nickel, and most preferably, palladium. The Group 8 metal may exist in any oxidation state ranging from the zero-valent state to any higher variance available to the metal.

Methods for preparing the aforementioned catalysts are known to those skilled in the art. For a description of general synthetic techniques, see *Inorganic Synthesis: Reagents for Transition Metal Complex and Organometallic Systems*; R. J. Angelici, Ed., Wiley-Interscience: New York, 1990, Vol. 28, pp. 77–135 (Chapter 2), incorporated herein by reference, wherein representative preparations of Group 8 complexes containing chelating amine, phosphine, and arsine ligands are taught.

As an alternative embodiment of this invention, the catalyst may be anchored or supported on a catalyst support, including a refractory oxide, such as silica, alumina, titania, or magnesia; or an aluminosilicate clay, or molecular sieve or zeolite; or an organic polymeric resin.

Heretofore, the transition metal catalyst has been described as comprising a transition metal and $P(t-Bu)_3$ as the ligand. It is not precisely known, however, whether the donor atoms of the ligand are bound to the transition metal during the entire process of this invention, or whether the ligand is in a labile or non-bonded configuration relative to the transition metal during part or all of the process. Generally, it is believed that the ligand is bonded to the transition metal; however, such a theory should not be binding upon the invention in any manner. Modern analytical techniques, such as nuclear magnetic resonance spectroscopy ($^{13}C$, $^{1}H$, $^{31}P$), infrared and Raman spectroscopies, and X-ray diffraction, may assist in the determination of initial catalyst structure and changes in structure throughout the process.

The transition metal catalyst may be synthesized first and thereafter employed in the arylation process. Alternatively, the catalyst can be prepared in situ in the arylation reaction mixture. If the latter mixture is employed, then a Group 8 catalyst precursor compound and the $P(t-Bu)_3$ are independently added to the reaction mixture wherein formation of the transition metal catalyst occurs in situ. Suitable precursor compounds include alkene and diene complexes of the Group 8 metals, preferably, di(benzylidene)acetone (dba) complexes of the Group 8 metals, as well as, monodentate phosphine complexes of the Group 8 metals, and Group 8 carboxylates. In the presence of $P(t-Bu)_3$ as the ligand, in situ formation of the transition metal catalyst occurs. Non-limiting examples of suitable precursor compounds include [bis-di(benzylidene)acetone]palladium (0), tetrakis-(triphenylphosphine)-palladium (0), tris-[di(benzylidene) acetone]palladium (0), tris-[di(benzylidene) acetone]-dipalladium (0), palladium acetate, and the analogous complexes of iron, cobalt, nickel, ruthenium, rhodium, osmium, iridium, and platinum.

Any of the aforementioned catalyst precursors may include a solvent of crystallization. Group 8 metals supported on carbon, preferably, palladium on carbon, can also be suitably employed as a precursor compound. Preferably, the catalyst precursor compound is bis-[di(benzylidene) acetone] palladium(0)

The quantity of transition metal catalyst which is employed in the process of this invention is any quantity which promotes the formation of the N-aryl amine product. Generally, the quantity is a catalytic amount, which means that the catalyst is used in an amount which is less than stoichiometric relative to the arylating agent. Typically, the transition metal catalyst ranges from about 0.01 to about 20 mole percent, based on the number of moles of amine compound used in the reaction. Preferably, the quantity of transition metal catalyst ranges from about 1 to about 10 mole percent, and more preferably from about 1 to about 4 mole percent, based on the moles of amine compound. In addition, the ratio of $P(t-Bu)_3$ ligand to Group 8 metal is preferably in the range from about 3:1 to about 0.25:1, more preferably from about 0.5:1 to about 2:1, and most preferably from about 0.8:1 to about 2:1.

The process described herein may be conducted in any conventional reactor designed for catalytic processes. Continuous, semi-continuous, and batch reactors can be employed. If the catalyst is substantially dissolved in the reaction mixture as in homogeneous processes, then batch reactors, including stirred tank and pressurized autoclaves, can be employed. If the catalyst is anchored to a support and is substantially in a heterogeneous phase, then fixed-bed and fluidized bed reactors can be used. In the typical practice of this invention the amine compound, arylating compound, base, and catalyst are mixed in batch, optionally with a solvent, and the resulting mixture is maintained at a temperature and pressure effective to prepare the N-arylated amine product.

Any solvent can be used in the process of the invention provided that it does not interfere with the formation of the N-aryl product. Both aprotic and protic solvents and combinations thereof are acceptable. Suitable aprotic solvents include, but are not limited to, aromatic hydrocarbons, such as toluene and xylene, chlorinated aromatic hydrocarbons, such as dichlorobenzene, and ethers, such as tetrahydrofuran. Suitable protic solvents include, but are not limited to, water and aliphatic alcohols, such as ethanol, isopropanol, and cyclohexonol, as well as glycols and other polyols. The amount of solvent which is employed may be any amount, preferably an amount sufficient to solubilize, at least in part, the reactants and base. A suitable quantity of solvent typically ranges from about 1 to about 100 grams solvent per gram reactants. Other quantities of solvent may also be suitable, as determined by the specific process conditions and by the skilled artisan.

Generally, the reagents may be mixed together or added to a solvent in any order. Air is preferably removed from the reaction vessel during the course of the reaction, however this step is not always necessary. If it is desirable or necessary to remove air, the solvent and reaction mixture can be sparged with a non-reactive gas, such as nitrogen, helium, or argon, or the reaction may be conducted under anaerobic conditions. The process conditions can be any operable conditions which yield the desired N-aryl product. Beneficially, the reaction conditions for this process are mild. For example, a preferred temperature for the process of the present invention ranges from about ambient, taken as about 22° C., to about 150° C., and preferably, from about 25° C. to about 70° C. The process may be run at subatmospheric pressures if necessary, but typically proceeds sufficiently well at about atmospheric pressure. The process is generally run for a time sufficient to convert as much of the amine compound to product as possible. Typical reaction times range from about 30 minutes to about 24 hours, but longer times may be used if necessary.

The N-arylated amine product can be recovered by conventional methods known to those skilled in the art, including, for example, distillation, crystallization, sublimation, and gel chromatography. The yield of product will vary depending upon the specific catalyst, reagents, and process conditions used. For the purposes of this invention, "yield" is defined as the mole percentage of N-aryl amine product recovered, based on the number of moles of amine or arylating compound employed. Typically, the yield of N-aryl amine product is greater than about 25 mole percent. Preferably, the yield of N-aryl amine product is greater than about 60 mole percent, and more preferably, greater than about 75 mole percent.

The following examples are intended to illustrate, but in no way limit the scope of the present invention. All parts and percentages are by weight and all temperatures are in degrees Celsius unless explicitly stated otherwise.

EXAMPLES 1–26

General Procedures:

All reactions were assembled in the drybox in sealed reaction vessels and were reacted either at room temperature or were heated in an oil bath. Toluene solvent was distilled from sodium/benzophenone ketyl. Diethylene glycol dimethylether was purchased in anhydrous grade from Aldrich and was used in the drybox. Palladium bis(dibenzylideneacetone) was prepared according to literature procedures1 and the palladium content was determined by elemental analysis. Sodium t-butoxide, potassium phosphate, and cesium carbonate were purchased from Aldrich and were used in a drybox. Sodium phenoxide was prepared by deprotonation of phenol with sodium hydride in THF followed by precipitation with pentane. All amines were used as received and were not degassed prior to use. General Prodecure for the Reaction of Amines with Aryl Halides:

In a dry box, aryl halide (1.00–1.10 mmol), amine (1.00 mmol), Pd(dba)$_2$ or Pd(OAc)$_2$ (0.01–0.02 mmol), tri-t-butylphosphine (1.6–3.2 mg, 0.008–0.016 mmol, 0.8 eq/Pd), and sodium tert-butoxide (144 mg, 1.50 mmol) were weighed directly into a screw cap vial. A stir bar was added followed by 1.0–2.0 mL of toluene to give a purple mixture. The vial was removed from the dry box and the mixture was stirred at room temperature. The reaction was monitored by thin layer chromatography or GC. After complete consumption of starting materials, the resulting thick brown suspension was adsorbed onto silica gel and purified by flash chromatography.

Triphenylamine (Paine, A. J. J. Am. Chem. Soc. 109:1496–1502 (1987)). The above general procedure was followed using bromobenzene (171 mg, 1.10 mmol) and diphenylamine (169 mg, 1.00 mmol) with 1 mol % Pd(dba)$_2$ and 0.8 mol % tri-t-butylphosphine in 1.0 mL of toluene. After one hour, the reaction mixture was adsorbed onto silica gel and chromatographed using 5% ethyl acetate/hexanes to give 236 mg (91%) of triphenyamine as a white solid. $^1$H NMR (500 MHz, C$_6$D$_6$) δ 7.17–6.99 (m, 12 H), 6.82 (t, J=7.2 Hz, 3H). $^{13}$C NMR (125 MHz, C$_6$D$_6$) δ 148.4, 129.5, 124.6, 122.9.

N-(2-Tolyl)diphenylamine (Nelson, R. F., et al., J. Am. Chem. Soc. 90:3925–3930 (1968)). The above general procedure was followed using 2-bromotoluene (188 mg, 1.10 mmol) and diphenylamine (169 mg, 1.00 mmol) with 1 mol % Pd(dba)$_2$ and 0.8 mol % tri-t-butylphosphine in 1.5 mL of toluene. After four hours, the reaction mixture was adsorbed onto silica gel and chromatographed with 2.5% ethyl acetate/hexanes to give 247 mg (95%) of N-(2-tolyl)diphenylamine as a colorless oil that crystallized to a white solid. $^1$H NMR (500 MHz, C$_6$D$_6$) δ 7.05–6.96 (m, 12 H), 6.78 (tt, J=7.25, 1.30 Hz, 2H), 1.99 (s, 3H). $^{13}$C NMR (125 MHz, C$_6$D$_6$) δ 148.0, 146.0, 136.6, 132.0, 129.9, 129.4, 127.7, 126.1, 122.0, 121.8, 18.7.

N-(4-Cyanophenyl)diphenylamine (Nelson, R. F., et al., J. Am. Chem. Soc. 90:3925–3930 (1968)). The above general procedure was followed using 4-bromobenzonitrile (188 mg, 1.03 mmol) and diphenylamine (169 mg, 1.00 mmol) with 1 mol % Pd(dba)$_2$ and 0.8 mol % tri-t-butylphosphine in 1.5 mL of toluene. After one hour, the reaction mixture was adsorbed onto silica gel and chromatographed with 50% toluene/hexanes to give 263 mg (97%) of N-(4-cyanophenyl)diphenylamine as a white solid. $^1$H NMR (500 MHz, C$_6$D$_6$) δ 6.97 (t, J=8 Hz, 4H), 6.92 (d, J=8.9 Hz, 2H), 6.86–6.83 (m, 6H), 6.56 (d, J=8.7 Hz, 2H). $^{13}$C NMR (125 MHz, C$_6$D$_6$) δ 151.3, 146.6, 133.2, 129.9, 126.1, 124.9, 120.5, 119.4, 104.0.

The above general procedure was followed using 4-chlorobenzonitrile (138 mg, 1.00 mmol) and diphenylamine (169 mg, 1.00 mmol) with 1 mol % Pd(dba)$_2$ and 0.8 mol % tri-t-butylphosphine in 2.0 mL of toluene. After 5.5 hours, the reaction mixture was adsorbed onto silica gel and chromatographed with 50% toluene/hexanes to give 242 mg (90%) of N-(4-cyanophenyl)diphenylamine as a white solid.

Tri(4-methoxyphenyl)amine (Walters, R. I. J. Am. Chem. Soc. 77:5999–6002 (1955)). The above general procedure was followed using 4-bromoanisole (187 mg, 1.00 mmol) and di(4-methoxyphenyl)amine (229 mg, 1.00 mmol) with 1 mol % Pd(dba)$_2$ and 0.8 mol % tri-t-butylphosphine in 1.5 mL of toluene. After one hour, the reaction mixture was adsorbed onto silica gel and chromatographed with 5% ethyl acetate/hexanes to give 321 mg (96%) of tri(4-methoxyphenyl)amine as a white solid. $^1$H NMR (500 MHz, C$_6$D$_6$) δ 7.08 (d, J=10 Hz, 6 H), 6.73 (d, J=10 Hz, 6H), 3.31 (s, 9H). $^{13}$C NMR (125 MHz, C$_6$D$_6$) δ 155.7, 142.6, 125.3, 115.0, 55.0.

N,N,N',N'-Tetraphenyl-1,4-phenylenediamine (Paine, A. J. J. Am. Chem. Soc. 109:1496–1502 (1987)). The above general procedure was followed using 1,4-dibromobenzene (130 mg, 0.55 mmol) and diphenylamine (169 mg, 1.00 mmol) with 1 mol % Pd(dba)$_2$ and 0.8 mol % tri-t-butylphosphine in 1.5 mL of toluene. After one hour, the reaction mixture was adsorbed onto silica gel and chromatographed using 30% toluene/hexanes to give 200 mg (97%) of N,N,N',N',-tetraphenyl-1,4-phenylenediamine as a white solid. This solid was recrystallized from ethy acetate to afford 168 mg (81%). $^1$H NMR (500 MHz, C$_6$D$_6$) δ 7.10 (d, J=7.5 Hz, 8H), 7.03 (t, J=8 Hz, 8H), 6.95 (s, 4H), 6.81 (t, J=7.2 Hz, 4H). $^{13}$C NMR (125 MHz, C$_6$D$_6$) δ 148.4, 143.4, 129.6, 125.8, 124.2, 122.8.

Diphenylamine. The above general procedure was followed using bromobenzene (157 mg, 1.00 mmol) and aniline (93 mg, 1.00 mmol) with 1 mol % Pd(dba)$_2$ and 0.8 mol % tri-t-butylphosphine in 1.5 mL of toluene. After one hour, the reaction mixture was adsorbed onto silica gel and chromatographed with 5% ethyl acetate/hexanes to give 145 mg (86%) of diphenylamine as a grey solid. $^1$H NMR (500 MHz, C$_6$D$_6$) δ 7.11–7.08 (m, 4H), 6.85–6.80 (m, 6H), 4.97 (br s, 1H). 13C NMR (125 MHz, C$_6$D$_6$) δ 143.6, 129.5, 121.1, 118.2. In addition, 21 mg (8%) of triphenylamine was isolated.

The above general procedure was followed using chlorobenzene (135 mg, 1.20 mmol) and aniline (93 mg, 1.00 mmol) with 5 mol % Pd(dba)$_2$ and 4 mol % tri-t-butylphosphine in 2.0 mL of toluene. After 25 hours, the reaction mixture was adsorbed onto silica gel and chromatographed with 2.5% ethyl acetate/hexanes to give 126 mg (75%) of diphenylamine as an off-white solid.

N-(4-Methoxyphenyl)diphenylamine (Paine, A. J. J. Am. Chem. Soc. 109:1496–1502 (1987)). The above general procedure was followed using 4-chloroanisole (127 mg, 1.00 mmol) and diphenylamine (169 mg, 1.00 mmol) with 5 mol % Pd(dba)$_2$ and 4 mol % tri-t-butylphosphine in 2.0 mL of toluene. After 16 hours at 70° C. the reaction mixture was adsorbed onto silica gel and chromatographed with 2% ethyl acetate/hexanes to give 267 mg (97%) of N-(4-methoxyphenyl)diphenylamine as a white solid. $^1$H NMR (500 MHz, $C_6D_6$) δ 7.10–6.99 (m, 10 H), 6.81 (t, J=7 Hz, 2H), 6.66 (d, J=8.8 Hz, 2H), 3.28 (s, 3H). $^{13}C$ NMR (125 MHz, $C_6D_6$) δ 156.8, 148.8, 141.2, 129.4, 127.7, 123.4, 122.2, 115.2, 54.94.

N-(2-methylphenyl)morpholine (Barluenga, J. et al., Chem. Eur. J. 3:1629–1637 (1997)). The above general procedure was followed using 2-bromotoluene (171 mg, 1.10 mmol) and morpholine (87 mg, 1.00 mmol) with 1 mol % Pd(OAc)$_2$ and 0.8 mol % tri-t-butylphosphine in 1.0 mL of toluene. After 6 hours, the reaction mixture was adsorbed onto silica gel and chromatographed using 5% ethyl acetate/hexanes to give 179 mg (>99%) of N-(2-methylphenyl)morpholine. $^1H$ NMR (500 MHz, CDCl$_3$) δ 7.20 (d J=7.4 Hz, 1H), 7.18 (d, J=7.4 Hz, 1H), 7.03 (d, J=7.4 Hz, 1H), 7.01 (d, J=7.4 Hz, 1H), 3.86 (t, J=4.5 Hz, 4H), 2.92 (t, J=4.5 Hz, 4H), 2.33 (s, 3H). $^{13}C$ NMR (125 MHz, CDCl$_3$) δ 151.4, 132.7, 131.2, 126.7, 123.5, 119.0, 67.5, 52.4, 17.8.

N-(4-methoxyphenyl)-N-methylaniline (Wolfe et al., J. Am. Chem. Soc. 119:6054–6058 (1997)). The above general procedure was followed using 4-bromoanisole (187 mg, 1.00 mmol) and N-methylaniline (107 mg, 1.00 mmol) with 1 mol % Pd(dba)$_2$ and 0.8 mol % tri-t-butylphosphine in 1.0 mL of toluene. After 6 hours, the reaction mixture was adsorbed onto silica gel and chromatographed with 5% ethyl acetate/hexanes to give 218 mg (>99%) of N-(4-methoxyphenyl)-N-methylaniline. $^1H$ NMR (500 MHz, CDCl$_3$) δ 7.21 (dd, J=8.9, 7.0 Hz, 2H), 7.12 (d, J=8.8 Hz, 2H), 6.91 (d, J=8.8 Hz, 2H), 6.81 (d, J=8.4 Hz, 2H), 6.80 (t, J=7.0 Hz, 1H), 3.83 (s, 3H), 3.28 (s, 3H). $^{13}C$ NMR (125 MHz, CDCl$_3$) δ 156.3, 149.8, 142.4, 128.9, 126.1, 118.5, 115.9, 114.8, 55.5, 40.4.

N-(4-cyanophenyl)-N-methylaniline (Marcoux, J. F. J. Org. Chem. 62:1568–1569 (1997)). The above general procedure was followed using 4-bromobenzonitrile (187 mg, 1.00 mmol) and N-methylaniline (107 mg, 1.00 mmol) with 1 mol % Pd(dba)$_2$ and 0.8 mol % tri-t-butylphosphine in 1.0 mL of toluene. After 6 hours, the reaction mixture was adsorbed onto silica gel and chromatographed with 10% ethyl acetate/hexanes to give 201 mg (97%) of N-(4-cyanophenyl)-N-methylaniline. $^1H$ NMR (500 MHz, CDCl$_3$) δ 7.45–7.42 (m, 4H), 7.27 (t, J=7.5 Hz, 1H), 7.21 (d, J=8.3 Hz, 2H), 6.73 (d, J=9.0 Hz, 2H), 3.36 (s, 3H). $^{13}C$ NMR (125 MHz, CDCl$_3$) δ 152.0, 146.8, 133.1, 130.1, 126.4, 126.2, 120.2, 114.0, 99.4, 40.1.

The above general procedure was followed using 4-chlorobenzonitrile (137 mg, 1.00 mmol) and N-methylaniline (107 mg, 1.00 mmol) with 1 mol % Pd(dba)$_2$ and 0.8 mol % tri-t-butylphosphine in 1.0 mL of toluene. After 12 hours, the reaction mixture was adsorbed onto silica gel and chromatographed with 10% ethyl acetate/hexanes to give 191 mg (92%) of N-(4-cyanophenyl)-N-methylaniline.

N,N-Dibutyl-p-toluidine (Watanabe, Y. et al., J. Org. Chem. 50:1365–1370. The above general procedure was followed using 4-bromotoluene (171 mg, 1.00 mmol) and dibutylamine (129 mg, 1.00 mmol) with 1 mol % Pd(dba)$_2$ and 0.8 mol % tri-t-butylphosphine in 1.0 mL of toluene. After 4 hours, the reaction mixture was adsorbed onto silica gel and chromatographed with 2% ethyl acetate/hexanes to give 207 mg (95%) of N,N-dibutyl-p-toluidine. $^1H$ NMR (500 MHz, CDCl$_3$) δ 7.01 (d, J=8.7 Hz, 2H), 6.58 (d, J=8.7 Hz, 2H), 3.23 (t, J=7.6 Hz, 4H), 2.24 (s, 3H), 1.58–1.52 (m, 4H), 1.34 (sept, J=7.4 Hz, 4H), 0.95 (t, J=7.4 Hz, 6H). $^{13}C$ NMR (125 MHz, CDCl$_3$) δ 146.4, 129.7, 124.5, 112.5, 51.1, 29.6, 20.5, 20.2, 14.0.

The above general procedure was followed using 4-chlorotoluene (126 mg, 1.00 mmol) and dibutylamine (129 mg, 1.00 mmol) with 1 mol % Pd(dba)$_2$ and 0.8 mol % tri-t-butylphosphine in 1.0 mL of toluene. After 4 hours at 70° C., the reaction mixture was adsorbed onto silica gel and chromatographed with 2% ethyl acetate/hexanes to give 196 mg (90%) of N,N-dibutyl-p-toluidine.

N,N-Dibutyl-p-toluidine using Cs$_2$CO$_3$ or K$_3$PO$_4$ as base. The above general procedure was followed using 4-bromotoluene (171 mg, 1.00 mmol) and dibutylamine (162 mg, 1.25 mmol) with 5 mol % Pd(dba)$_2$, 4 mol % tri-t-butylphosphine, and cesium carbonate (489 mg, 1.50 mmol) or potassium phosphate (318 mg, 1.5 mmol) in 1.0 mL of diglyme. After 12 hours at 100° C., the reaction mixture was adsorbed onto silica gel and chromatographed with 2% ethyl acetate/hexanes to give 179 mg (82%) of N,N-dibutyl-p-toluidine with Cs$_2$CO$_3$, or 193 mg (88%) with K$_3$PO$_4$.

N,N-Dibutyl-o-toluidine (Watanabe, Y. et al., Bull. Chem. Soc., Jpn., 55:1116–1120 (1982)). The above general procedure was followed using 2-bromotoluene (171 mg, 1.00 mmol) and dibutylamine (129 mg, 1.00 mmol) with 2 mol % Pd(OAc)$_2$ and 1.6 mol % tri-t-butylphosphine in 1.0 mL of toluene. After 6 hours, the reaction mixture was adsorbed onto silica gel and chromatographed with 2% ethyl acetate/hexanes to give 181 mg (83%) of N,N-dibutyl-o-toluidine. $^1H$ NMR (500 MHz, CDCl$_3$) δ 7.18 (t, J=7.8 Hz, 1H), 7.13 (d, J=7.8 Hz, 1H), 7.08 (d, J=7.8 Hz, 1H), 6.97 (t, J=7.8 Hz, 1H), 2.91 (t, J=7.5 Hz, 4H), 2.30 (s, 3H), 1.41–1.37 (m, 4H), 1.27 (sept, J=7.3 Hz, 4H), 0.87 (t, J=7.3 Hz, 6H). $^{13}C$ NMR (125 MHz, CDCl$_3$) δ 150.7, 135.0, 130.9, 126.0, 123.1, 122.3, 53.9, 29.6, 20.5, 18.3, 14.0.

General procedure for reaction of azoles with aryl halides. In a dry box, aryl halide (1.00–1.20 mmol), azole (1.00 mmol), Pd(dba)$_2$ (17–23 mg, 0.03–0.04 mmol, 3–4 mol %), tri-t-butylphosphine (4.8–8.1 mg, 0.024–0.040 mmol, 0.8–1.0 eq/Pd), and cesium carbonate (489–554 mg, 1.50–1.70 mmol) were weighed directly into a one dram screw cap vial. A stir bar was added followed by 1.0–2.0 mL of toluene. The vial was removed from the dry box and the mixture was stirred as rapidly as possible with a magnetic stir plate in an oil bath heated to 100° C. The reaction was monitored by GC and after the consumption of starting materials, the reaction mixture was adsorbed onto silica gel and purified by chromatography.

N-(4-fluorophenyl)-5-methoxyindole (Perregaard, J., J. Med. Chem. 35:1092–1101 (1992)). The above general procedure was followed using 4-flouorobromobenzene (210 mg, 1.20 mmol), 5-methoxyindole (147 mg, 1.00 mmol), 4 mol % Pd(dba)$_2$, 4 mol % tri-t-butylphosphine, and cesium carbonate (1.70 mmol) in 1.0 mL of toluene. After 12 hours at 100° C., the reaction mixture was adsorbed onto silica gel and chromatographed with 5% ethyl acetate/hexanes to give 212 mg (88%) of N-(4-fluorophenyl)-5-methoxyindole. Recrystallization from 5% ethyl acetate/hexanes gave 174 mg (72%) of pure product. $^1H$ NMR (300 MHz, CDCl$_3$) δ 7.49–7.39 (m, 3H), 7.28 (d, J=3.2 Hz, 1H), 7.22 (t, J=8.6 Hz, 1H), 7.18 (d, J=2.3 Hz, 1H), 6.93 (dd, J=9.0, 1.6 Hz, 1H), 6.64 (d, J=3.1 Hz, 1H), 3.90 (s, 3H). 13C NMR (76 Mz, CDCl$_3$) δ 160.9 (d, J=244.0 Hz) 154.4, 136.0, 131.3, 129.7, 128.4, 125.76 (d, J=8.5 Hz), 116.38 (d, J=23 Hz), 112.6, 11.0, 103.2, 102.7, 55.76.

N-(2-methylphenyl)-3-methylindole. The above general procedure was followed using 2-bromotoluene (205 mg, 1.20 mmol), 3-methylindole (131 mg, 1.00 mmol), 3 mo % Pd(dba)2, 2.4 mol % tri-t-butylphosphine, and cesium carbonate (1.70 mmol) in 1.0 mL of toluene. After 12 hours at 100° C., the reaction mixture was adsorbed onto silica gel and chromatographed with 5% ethyl acetate/hexanes to give 195 mg (88%) of N-(2-methylphenyl)-3-methylindole. $^1$H NMR (300 MHz, CDCl$_3$) δ 7.76 (m, 1H), 7.46 (m, 2H), 7.40 (m, 2H), 7.28 (m, 2H), 7.15 (m, 1H), 7.06 (s, 1H), 2.53 (S, 3H), 2.21 (s, 3H). $^{13}$C NMR (76 MHz, CDCl$_3$) δ 138.4, 137.1, 135.7, 131.1, 128.6, 128.1, 127.8, 126.6, 126.2, 121.9, 119.3, 118.9, 111.6, 110.4, 17.7, 9.6.

N-(4-methoxyphenyl)indole (Tokmakov, G. P. et al., Tetrahedron 51:2091–2098 (1995). The above general procedure was followed using bromoanisole (138 μL, 1.10 mmol) and indole (119 mg, 1.02 mmol) with 3 mol % Pd(dba)$_2$, 3 mo % tri-t-butylphosphine and cesium carbonate (1.70 mmol) in 2 mL of toluene. After 6 hours at 100° C., the reaction mixture was adsorbed onto silica gel and flash chromatographed with 5% ethyl acetate/hexanes to give 163 mg (72%) of product as a colorless oil which was pure by $^1$H NMR. Recrystallization from ethanol gave a white, crystalline solid. mp 59.5–60.5° C. (Lit. mp 57–58° C.). $^1$H NMR (500 MHz, CDCl$_3$) δ 7.74 (d, J=7.84 Hz, 1H), 7.52 (d, J=7.93 Hz, 1H), 7.45 (d, J=7.80 Hz, 2H), 7.32 (d, J=3.4 Hz, 2H), 7.26 (t, J=6.90 Hz, 1H), 7.21 (t, J=7.40 Hz, 1H), 7.08 (d, J=8.01 Hz, 2H), 6.71 (d, J=3.11 Hz, 2H), 3.91 (s, 3H). $^{13}$C NMR (125 MHz, CDCl$_3$) δ 158.2, 136.3, 132.8, 128.9, 128.2, 125.9, 22.1, 121.0, 120.0, 114.7, 110.3, 102.8, 55.5.

N-(4-methylphenyl)pyrrole (Jones, R. A. Aust. J. Chem. 19:289–296 (1966)). The above general procedure was followed using bromotoluene (135 μL, 1.10 mmol) and pyrrole (69 μL, 1.00 mmol) with 3 mol % Pd(dba)$_2$, 3 mol % tri-t-butylphosphine, and cesium carbonate (1.70 mmol) in 2.0 mL toluene. After heating at 100° C. for 6 hours, the reaction mixture was loaded on silica gel and flash chromatographed with 2.5% ethyl acetate/hexanes to give 135 mg (86%) of product as a pinkish solid which was pure by $^1$H NMR. Recrystallization from ethanol gave a colorless, crystalline solid. mp 81.5–83° C. (lit. mp 82–83° C.). $^1$H NMR (500 MHz, CDCl$_3$) δ 7.30 (d, J=8.15 Hz, 2H), 7.23 (d, J=8.44 Hz, 2H), 7.08 (brs, 2H), 6.36 (brs, 2H), 2.40 (s, 3H). $^{13}$C NMR (125 MHz, CDCl$_3$) δ 138.5, 135.3, 130.0, 120.5, 119.4, 110.0, 20.8.

N-(4-methylphenyl)indole (Watanabe, Y. et al., Bull. Chem. Soc., Jpn., 55:1116–1120 (1982)). The above general procedure was followed using of 4-chlorotoluene (126 mg, 1.00 mmol), indole (117 mg, 1.00 mmol), 4 mol % Pd(dba)$_2$, 4 mol % tri-t-butylphosphine, and cesium carbonate (1.50) in 1.0 mL of toluene. After 12 hours at 100° C., the reaction mixture was adsorbed onto silica gel and chromatographed with 10% ethyl acetate/hexanes to give 137 mg (66%) of N-(4-methylphenyl)indole. $^1$H NMR (500 MHz, CDCl$_3$) δ 7.70 (d, J=7.8 Hz, 1H), 7.54 (d, J=8.2 Hz, 1H), 7.40 (d, J=7.8 Hz, 2H), 7.34–7.33 (m, 3H), 7.23 (t, J=7.8 Hz, 1H), 7.18 (t, J=7.8 Hz, 1H), 5 6.68 (d, J=2.4 Hz, 1H), 2.46 (s, 3H). $^{13}$C NMR (125 MHz, CDCl$_3$) δ 137.4, 136.4, 136.1, 130.2, 129.3, 128.2, 124.4, 122.3, 121.2, 120.3, 110.6, 103.3, 21.1.

General procedure for carbamate arylation: In a drybox, a small round bottom was charged with Pd(dba)$_2$ (14.4 mg, 0.025 10 mmol, 2.5 mol %), t-BU$_3$P (10.1 mg, 0.050 mmol), sodium phenoxide (174 mg, 1.50 mmol), aryl halide (1.00 mmol), and t-butyl carbamate (176 mg, 1.50 mmol). Toluene (3 mL) was added to give a thick suspension. The flask was sealed with a septum, removed from the drybox, and placed in an oil bath preheated to 100° C. The reaction was vigorously stirred until the aryl halide was completely consumed as judged by GC analysis. The reaction was then worked up as described below. The pure product was obtained by flash chromatography.

t-Butyl N-(4-tolyl)carbamate (Stanley, R. L. et al., J. Org. Chem. 42:3686–3690 (1977)). The above general procedure was followed using 4-bromotoluene (123 μL, 1.00 mmol). After 2 hours, the toluene was removed under reduced pressure and the residue loaded on silica gel. The crude material was flash chromatographed eluting with 1:1 CH$_2$Cl$_2$:hexanes (150 mL) then 70:30 CH$_2$Cl$_2$:hexanes. Isolated 177 mg (85%) of a pale yellow oil that crystallized upon standing. Recrystallization from hexanes gave colorless needles. mp 92–92.5° C. (lit. mp 91–93° C.) $^1$H NMR (500 MHz, CDCl$_3$) δ 7.24 (br d, 8.3 Hz, 2H), 7.10 (d, J=8.2 Hz, 2H), 6.41 (br s, 1H), 2.30 (s, 3H), 1.52 (s, 9H). $^{13}$C NMR (125 MHz, CDCl$_3$) δ 152.9, 135.7, 132.5, 129.4, 118.7, 80.3, 28.3, 20.7. FTIR (KBr disc): 3356, 1699, 1529, 1240, 1157 cm$^{-1}$.

The above general procedure was followed using 4-chlorotoluene (118 μL, 1.00 mmol), 4 mol % Pd(dba)$_2$, and 8 mol % tri-t-butylphosphine. After 24 hours, t-Butyl N-(4-tolyl)carbamate was isolated as described above to give 122 mg (59% yield) of product.

t-Butyl N-(2-tolyl)carbamate (Muchowski, J. M. et al., J. Org. Chem. 45:4798–4801 (1980)). The above general procedure was followed using 2-bromotoluene (120 μL, 1.00 mmol). After 2 hours, the toluene was removed under reduced pressure and the residue loaded on silica gel. The crude material was flash chromatographed eluting with 1:1 CH$_2$Cl$_2$:hexanes. Isolated 178 mg (86%) of a pale yellow oil which crystallized upon standing.

Recrystallization from hexanes gave colorless needles. mp 82–83° C. (lit. mp 82° C.). $^1$H NMR (500 MHz, CDCl$_3$) δ 7.81 (br s, 1H), 7.20 (t, J=7.4 Hz, 1H), 7.15 (d, J=7.4 Hz, 1H), 6.99 (t, J=8.3 Hz, 1H), 6.27 (br s, 1H), 2.26 (s, 3H), 1.54 (s, 9H). $^{13}$C NMR (125 MHz, CDCl$_3$) δ 153.1, 136.4, 130.3, 127.3, 126.8, 123.7, 21.1, 80.4, 28.3, 17.6. FTIR (KBr disc): 3261, 1696, 1510, 371, 1155 cm$^{-1}$.

t-Butyl N-(4-cyanophenyl)carbamate. The above general procedure was followed using 4-bromobenzonitrile (186 mg, 1.02 mmol). After 1.5 hours, the reaction was diluted with CH$_2$Cl$_2$ and extracted with 10% NaOH solution to remove phenol which coelutes with the product. The organic layer was dried over MgSO$_4$ and the solvent removed under reduced pressure. The residue was flash chromatographed eluting with 70:30 CH$_2$Cl$_2$:hexanes (200 mL) then CH$_2$Cl$_2$. Isolated 193 mg (87%) of a pale yellow solid. Recrystallization from toluene/hexanes gave colorless needles. mp 120–120.5° C. $^1$H NMR (500 MHz, CDCl$_3$) δ 7.57 (d, J=8.6 Hz, 2H), 7.48 (d, J=8.6 Hz, 2H), 6.74 (br s, 1H), 1.53 (s, 9H). $^{13}$C NMR (125 MHz, CDCl$_3$) δ 151.9, 142.6, 133.2, 119, 118.1, 105.8, 81.7, 28.2. FTIR (KBr disc): 3368, 2226, 1692, 1510, 1239, 1151 cm$^{-1}$. Anal. Calculated for Cl$_2$H$_{14}$N$_2$O$_2$: C, 66.05; H, 6.47; N, 12.83. Found: C, 65.80; H, 6.43; N, 12.77.

t-Butyl N-(4-methoxyphenyl)carbamate (Kondo, T., Organometallics 17:2131–2134 (1998)). The above general procedure was followed using 4-bromoanisole (123 μL, 0.98 mmol), 4 mol % Pd(dba)$_2$, and 8 mol % tri-t-butylphosphine. Upon completion of the reaction, the reaction was diluted with CH$_2$Cl$_2$ and extracted with 10% NaOH solution to remove phenol which coelutes with the product. The organic layer was dried over MgSO$_4$ and the solvent removed under reduced pressure. The residue was flash chromatographed eluting with 70:30 CH$_2$Cl$_2$:hexanes. Isolated 145 mg (66%) of a pale yellow, waxy solid. Recrystallization from hexanes gave colorless needles. mp 92.5–93° C. (lit mp 92–94° C.). $^1$H NMR(500 MHz, CDCl$_3$) δ 7.28 (br s, 2H), 6.84 (d, J=9.4 Hz, 2H), 6.36 (br s, 1H), 3.79 (s, 3H), 1.52 (s, 9H). $^{13}$C NMR (125 MHz, CDCl$_3$) δ 155.5, 153.1, 131.4, 120.4, 114.0, 80.1, 55.4, 28.3. FTIR (KBr disc): 3365, 1694, 1522, 1246, 1161 cm$^{-1}$.

The room temperature amination of aryl bromides with arylamines and secondary alkylamines is provided in Table 1.

TABLE 1

Reactions of Aryl Halides with Amines Catalyzed by Pd(O)/P(t-u)$_3$

| Example | Arylating Compound | Amine Compound | Product | Cond.[1] | Yield[2] |
|---|---|---|---|---|---|
| 1 | PhBr | (Ph)$_2$NH | (Ph)$_3$N | 1% Pd, 1 h, RT | 91% |
| 2 | 2-MeC$_6$H$_4$Br | (Ph)$_2$NH | 2-MeC$_6$H$_4$NPh$_2$ | 1% Pd, 4 h, RT | 97% |
| 3 | 4-NC-C$_6$H$_4$Br | (Ph)$_2$NH | 4-NC-C$_6$H$_4$NPh$_2$ | 1% Pd, 1 h, RT | 97% |
| 4 | 4-MeO-C$_6$H$_4$Br | (4-MeO-C$_6$H$_4$)$_2$NH | (4-MeO-C$_6$H$_4$)$_3$N | 1% Pd, 1 h, RT | 94% |
| 5 | 1,4-Br$_2$C$_6$H$_4$ | (Ph)$_2$NH | 1,4-(Ph$_2$N)$_2$C$_6$H$_4$ | 1% Pd, 1 h, RT | 85% |
| 6 | PhBr | PhNH$_2$ | (Ph)$_2$NH | 1% Pd, 1 h, RT | 87% |
| 7 | 4-MeC$_6$H$_4$Br | HNBu$_2$ | 4-MeC$_6$H$_4$NBu$_2$ | 1% Pd, 4 h, RT | 90% |
| 8 | 2-MeC$_6$H$_4$Br | HNBu$_2$ | 2-MeC$_6$H$_4$NBu$_2$ | 2% Pd[3], 6 h, RT | 81% |
| 9 | 2-MeC$_6$H$_4$Br | morpholine | 2-Me-C$_6$H$_4$-morpholine | 1% Pd[3], 6 h, RT | 96% |
| 10 | 4-MeO-C$_6$H$_4$Br | PhNHMe | 4-MeO-C$_6$H$_4$NPhMe | 1% Pd[3], 6 h, RT | 99% |

TABLE 1-continued

Reactions of Aryl Halides with Amines Catalyzed by Pd(O)/P(t-u)₃

| Example | Arylating Compound | Amine Compound | Product | Cond.[1] | Yield[2] |
|---|---|---|---|---|---|
| 11 | 4-Br-C₆H₄-CN | PhNHMe | 4-(MePhN)-C₆H₄-CN | 1% Pd, 5 h, RT | 95% |
| 12 | 4-Cl-C₆H₄-CN | PhNHMe | 4-(MePhN)-C₆H₄-CN | 1% Pd, 12 h, RT | 90% |
| 13 | 4-Cl-C₆H₄-Me | HNBu₂ | 4-(Bu₂N)-C₆H₄-Me | 1% Pd, 12 h, 70° C. | 88% |
| 14 | 4-Cl-C₆H₄-CN | HNPh₂ | 4-(Ph₂N)-C₆H₄-CN | 1% Pd, 5.5 h, RT | 89% |
| 15 | C₆H₅-Cl | H₂NPh | HNPh₂ | 5% Pd, 25 h, RT | 75% |
| 16 | 4-Cl-C₆H₄-OMe | HNPh₂ | 4-(Ph₂N)-C₆H₄-OMe | 4% Pd, 16 h, 70° C. | 80% |

[1]Reactions run with 1 mmol of aryl halide in 1–2 mL of toluene solvent. Pd(dba)₂ used in combination with 0.8 equiv of ligand/Pd.
[2]Isolated yields are an average of at least two runs.
[3]Pd(OAc)₂ used as the catalyst precursor.

In most cases, the use of Pd(dba)₂ led to faster reactions than the use of Pd(OAC)₂. However, in the case of reacting ortho-substituted aryl bromides with secondary amines, reactions intiated with Pd(OAC)₂ were faster. In all cases, the room temperature chemistry was achieve by using 0.8 to 1 equivalent of ligand/Pd(dba)₂. The use of 4 equiv of ligand, or even 2 equiv in most cases, led to reactions that occurred at elevated temperatures. Reactions with diarylamines were the fastest, occurring within 15 minutes in some cases. Reactions of aniline with aryl bromines also occurred within hours at room temperature. In this case, small amounts of triarylamine were observed. Reactions with cyclic secondary amines were also rapid. Reactions with acyclic secondary amines occurred with unactivated aryl bromides within 6 h.

Systems with enolizable hydrogens, nitro groups or labile esters are incompatible with the strongly basic NaO-t-Bu. Buchwald and Wolfe (Wolfe et al., Tetrahedron Lett. 38:6359–6362 (1997)) previously reported conditions using Cs₂CO₃ for the amination of activated aryl bromides. Equation II shows that this class of reaction can be conducted under similar conditions to those employing the expensive ligand of Kumada and Hayashi when using a 0.8% P(t-BU)₃ and 1% Pd(dba)₂ as catalyst.

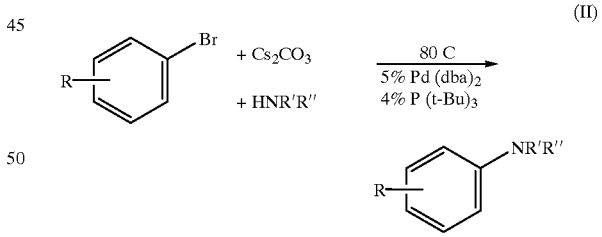

(II)

The use of aryl chlorides rather than bromides or iodides in cross-coupling chemistry has been actively pursued because of the low cost of these reagents (Ben-David, Y.; Portnoy, M.; Gozin, M.; Milstein, D. *Organometallics* 11:1995–1996 (1992); Grushin, V. V.; Alper, H. *Chem. Rev.* 94:1047–1062 (1994)). P(t-Bu)₃-complexes of palladium have allowed from Suzuki and Heck chemistry to be conducted with aryl chlorides (Littke, A. F.; Fu, G. C. *Agnew. Chem. Int. Ed. Eng.* 37:3387–3338 (1998); Littke, A. F.; Fu, G. C. *J. Org. Chem.* 64:10–11, 1999)) as well as palladium-catalyzed arylation of ketones and malonates (Old, D. W.; Wolfe, J. P.; Buchwald, S. L. *J. Am. Chem. Soc.* 120:9722–9823 (1998)). The optimized conditions for aromatic amination can be conducted at 70° C. with 1–3 mol % catalyst to allow for the formation of dialkyl anilines or triarylamines from unactivated aryl chlorides in yields that are similar to those observed at room temperature with bromides.

As shown in Table 1, some of the aryl chloride aminations occurred at room temperature. Reactions of 4-bromobenzonitrile was previously reported at room temperature, (Old et al., supra) but less activated aryl halides required heating. Surprisingly, chlorobenzene reacted with aniline at room temperature with 5 mol % catalyst over the course of 24 h in 75% yield. This is believed to be the first amination of an unactivated chloroarene at room temperature. The oxidative addition of aryl chlorides to $P(t\text{-}Bu)_3$-ligated Pd(0) is rapid.

The reductive elimination to form aryl amines, ethers and sulfides is sensitive to the nucleophilicity of the heteroatom bound to palladium (Hartwig, J. F. Acc. Chem. Res. 31:852–860 (1998)). For example, the reductive elimination of N-aryl azoles is slow (Mann, G.; Driver, M. S.; Hartwig, J. F. J. Am. Chem. Soc. 120:827–828 (1998)), and the reductive elimination of N-aryl carbamates is believed to not have been heretofore observed. Thus, optimized conditions with $P(t\text{-}Bu)_3$ as ligand might increase the scope of aromatic C—N bond formation to examples that are hampered by slow reductive elimination. This potential was realized as shown in Table 2.

TABLE 2

Reactions of Azoles and Carbamates Catalyzed by $Pd(O)/P(t\text{-}Bu)_3$

| Example | Arylating Compound | Amine Compound | Product | Cond.[4] | Yield[5] |
|---|---|---|---|---|---|
| 17 | | | | 4% Pd, 12 h | 72% |
| 18 | | | | 3% Pd, 12 h | 88% |
| 19 | | | | 3% Pd, 6 h | 83% |

TABLE 2-continued

Reactions of Azoles and Carbamates Catalyzed by Pd(O)/P(t-Bu)$_3$

| Example | Arylating Compound | Amine Compound | Product | Cond.[4] | Yield[5] |
|---|---|---|---|---|---|
| 20 | 4-bromotoluene | pyrrole | 1-(p-tolyl)pyrrole | 3% Pd, 6 h | 77% |
| 21 | 4-chlorotoluene | indole | 1-(p-tolyl)indole | 5% Pd, 12 h | 64% |
| 22 | 4-bromotoluene | H$_2$N-C(O)-OtBu | p-tolyl-HN-C(O)-OtBu | 2.5% Pd, 2 h | 80% |
| 23 | 4-chlorotoluene | H$_2$N-C(O)-OtBu | p-tolyl-HN-C(O)-OtBu | 4% Pd, 24 h | 59% |
| 24 | 2-bromotoluene | H$_2$N-C(O)-OtBu | o-tolyl-HN-C(O)-OtBu | 2.5% Pd, 2 h | 86% |

TABLE 2-continued

Reactions of Azoles and Carbamates Catalyzed by Pd(O)/P(t-Bu)₃

| Example | Arylating Compound | Amine Compound | Product | Cond.[4] | Yield[5] |
|---|---|---|---|---|---|
| 25 | 4-bromobenzonitrile (NC-C₆H₄-Br) | H₂N-C(O)-OtBu | HN(C(O)OtBu)-C₆H₄-CN | 2.5% Pd, 1.5 h | 83% |
| 26 | 4-bromoanisole (MeO-C₆H₄-Br) | H₂N-C(O)-OtBu | HN(C(O)OtBu)-C₆H₄-OMe | 4% Pd, 4 h | 62% |

[4] Reactions run with 1 mmol of azole and 1–1.2 mmol of aryl halide or 1 mol of aryl halide and 1.5 mmol t-butyl carbamate in 3 mL of toluene solvent at 100° C. For azole arylation, reactions were run with a 1:1 ratio of ligand to Pd(dba)₂; for carbamate arylation, reactions used 2.0 equiv of ligand/Pd.
[5] Isolated yields are an average of at least two runs.

The catalyst system involving P(t-Bu)₃ as ligand allowed for much milder arylation of azoles than the combination of Pd(OAc)₂ and DPPF reported previously (Mann, G.; Driver, M. S.; Hartwig, J. F. *J. Am. Chem. Soc.* 120:827–828 (1998)). The general reaction scheme is shown in Equation III.

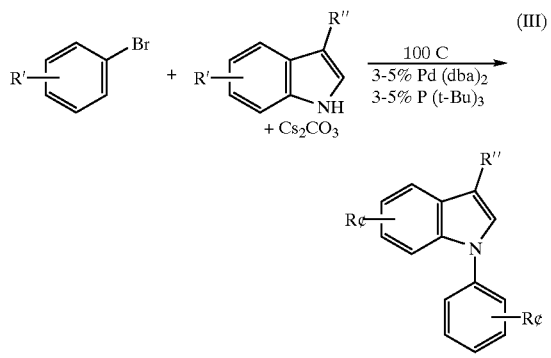

(III)

As shown in Table 2, the reaction between indole or pyrrole and unhindered aryl halides, either activated or unactivated, occurred at temperatures between 100° C. after 6–12 h. The use of Cs₂CO₃ as base, rather than NaO-t-Bu, was a significant factor in the success of the reactions. Hindered aryl halides such as 2-bromotoluene generated three reaction products, two of them isomeric monoaryl adducts and the second a diarylation product. The inventors assume that these products resulted from competing N- and C-arylations. Consistent with this hypothesis, the reaction of 3-methyl indole with 2-bromotoluene gave the N-aryl product in high yield. Thus, hindered aryl halides may be used when the 3-position of the indole is blocked. Reactions of chloroarenes with indoles also gave N-arylindoles, although in somewhat lower yield than the reactions of bromoarenes.

Finally, an optimized catalyst system allows for the use of a convenient ammonia equivalent, t-butylcarbamate, to form Boc-protected anilines from aryl halides as shown in Equation IV.

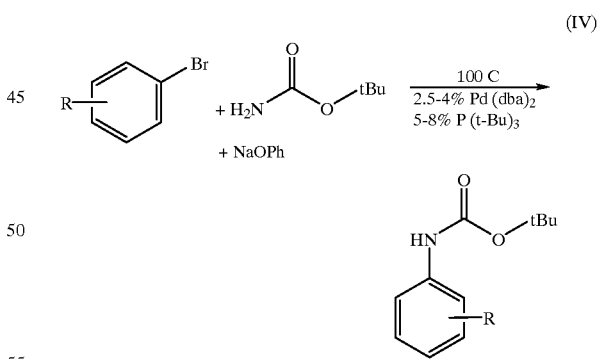

(IV)

In Equation IV, the use of NaoPh as base was crucial to the success of the reaction. Reactions that employed Cs₂CO₃ or NaO-t-Bu as base for the coupling of t-butylcarbamate with aryl bromides gave low conversions. In contrast to the C—N bond formations described above, the use of a 2:1 ratio of ligand palladium was optimal, presumably because oxidative addition is not rate determining in this coupling of carbamate. For these reactions, toluene proved to the most effective solvent.

Although the invention has been shown and described with respect to illustrative embodiments thereof, it should be appreciated that the foregoing and various other changes, omissions and additions in the form and detail thereof may be made without departing from the spirit and scope of the invention as delineated in the claims. All patents, patent applications, and publications mentioned herein are incorporated by reference in their entireties.

What is claimed is:

1. A process for the preparation of N-aryl amine compounds, comprising reacting an amine compound with an arylating compound in the presence of a base and a transition metal catalyst under reaction conditions effective to form an N-aryl amine compound, said transition metal catalyst comprising a Group 8 metal and P(t-Bu)$_3$ as a ligand, and wherein the ratio of said ligand to said Group 8 metal is in the range of about 3:1 to about 0.25:1, and wherein the reaction temperature is less than 100° C.

2. The process of claim 1, wherein said amine compound is selected from the group consisting of aryl amines, cyclic amines, secondary alkylamines, carbamates, and combinations thereof.

3. The process of claim 2, wherein said cyclic amine compound is an azole.

4. The process of claim 3, wherein said azole is selected from the group consisting of pyrrole, indole, and combinations thereof.

5. The process of claim 2, wherein said aryl amine comprises at least one substituted or unsubstituted phenyl group.

6. The process of claim 1, wherein said arylating compound is selected from those having the formula

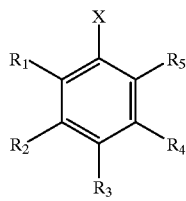

wherein X is a halogen atom or a sulfur-containing leaving group, and R$_1$, R$_2$, R$_3$, R$_4$, R$_5$ are independently selected from the group consisting of H, CN, alkyl, alkoxy, vinyl, alkenyl, formyl, CF$_3$, CCl$_3$, halide, C$_6$H$_5$, amide, acyl, ester, alkoxy, amino, thioalkoxy, phosphino, and combinations thereof.

7. The process of claim 6, wherein said sulfur-containing leaving group is selected from the group consisting of sulfonate, triflate, tosylate, and combinations thereof.

8. The process of claim 6, wherein said arylating compound is selected from those having the formula XC$_6$H$_4$R, wherein X is a halogen atom and R is selected from the group consisting of halogen, p-CN, p-t-Bu, m-OMe, o-Me, p-C(O)H, p-CF$_3$, p-Ph, p-C(O)NEt$_2$, p-H, and p-C(O)Ph.

9. The process of claim 1, wherein said base is selected from the group consisting of alkali metal hydroxides, alkali metal alkoxides, metal carbonates, alkali metal amides, alkali metal aryl oxides, tertiary amines, tetraalkylammonium hydroxides, diaza organic bases, and combinations thereof.

10. The process of claim 1, wherein said Group 8 metal is palladium, platinum, or nickel.

11. The process of claim 1, wherein said transition metal catalyst is prepared in situ in the reaction mixture.

12. The process of claim 11, wherein said transition metal catalyst is prepared from an alkene or diene complex of a Group 8 transition metal complex or a Group 8 transition metal carboxylate combined with said P(t-Bu)$_3$.

13. The process of claim 12, wherein the alkene complex of the Group 8 transition metal is di(benzylidene)acetone.

14. The process of claim 1, wherein said transition metal catalyst is present in said reaction in an amount from about 1 to about 10 mole percent, based on the total moles of said amine compound.

15. The process of claim 14, wherein said transition metal catalyst is present in said reaction in an amount from about 3 to about 8 mole percent, based on the total moles of said amine compound.

16. The process of claim 1, wherein the ratio of said ligand to said Group 8 metal is in the range of about 0.5:1 to about 2:1.

17. The process of claim 16, wherein the ratio of said ligand to said Group 8 metal is in the range of about 0.8:1 to about 2:1.

18. The process of claim 1, wherein said transition metal catalyst is anchored or supported on a support.

19. The process of claim 1, wherein said reaction conditions further comprise a solvent selected from the group consisting of aromatic hydrocarbons, chlorinated aromatic hydrocarbons, ethers, water, aliphatic alcohols, and combinations thereof.

20. The process of claim 1, further comprising the step of isolating said N-aryl amine compounds.

21. A process for the preparation of N-aryl amine compounds, comprising reacting an amine compound selected from the group consisting of aryl amines, cyclic amines, secondary alkylamines, carbamates, and combinations thereof, and an arylating compound in the presence of a base and a transition metal catalyst comprising a Group 8 metal and P(t-Bu)$_3$ as a ligand under reaction conditions effective to form an N-aryl amine compound, and wherein the ratio of said ligand to said Group 8 metal is in the range of about 3:1 to about 0.25:1, and wherein the reaction temperature is less than 100° C.

22. The process of claim 21, wherein said arylating compound is selected from those having the formula

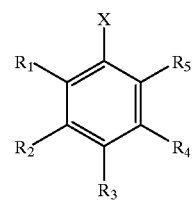

wherein X is a halogen atom or a sulfur-containing leaving group, and R$_1$, R$_2$, R$_3$, R$_4$, R$_5$ are independently selected from the group consisting of H, CN, alkyl, alkoxy, vinyl, alkenyl, formyl, CF$_3$, CCl$_3$, halide, C$_6$H$_5$, amide, acyl, ester, alkoxy, amino, thioalkoxy, phosphino, and combinations thereof.

23. The process of claim 22, wherein said sulfur-containing leaving group is selected from the group consisting of sulfonate, triflate, tosylate, and combinations thereof.

24. The process of claim 21, wherein said arylating compound is selected from those having the formula $XC_6H_4R$, wherein X is a halogen atom and R is selected from the group consisting of halogen, p-CN, p-t-Bu, m-OMe, o-Me, p-C(O)H, p-CF$_3$, p-Ph, p-C(O)NEt$_2$, p-H, and p-C(O)Ph.

25. The process of claim 21, wherein the ratio of said ligand to said Group 8 metal is in the range of about 0.5:1 to about 2:1.

26. The process of claim 25, wherein the ratio of said ligand to said Group 8 metal is in the range of about 0.8:1 to about 2:1.

* * * * *

UNITED STATES PATENT AND TRADEMARK OFFICE
CERTIFICATE OF CORRECTION

| | | |
|---|---|---|
| PATENT NO. | : 6,100,398 | Page 1 of 1 |
| APPLICATION NO. | : 09/343383 | |
| DATED | : August 8, 2000 | |
| INVENTOR(S) | : John F. Hartwig et al. | |

It is certified that error appears in the above-identified patent and that said Letters Patent is hereby corrected as shown below:

Column 1, line 14, "Award Number 1-R29-GM382-01" should be changed to -- Grant Number GM038201 --

Signed and Sealed this
Eighteenth Day of October, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 6,100,398 | Page 1 of 1 |
| APPLICATION NO. | : 09/343383 | |
| DATED | : August 8, 2000 | |
| INVENTOR(S) | : John F. Hartwig et al. | |

It is certified that error appears in the above-identified patent and that said Letters Patent is hereby corrected as shown below:

Column 1, line 12, delete the text under the heading "STATEMENT OF GOVERNMENT SUPPORT" as in the original patent and corrected by a previous certificate of correction and replace with the following:

---This invention was made with government support under GM038201 awarded by National Institutes of Health. The government has certain rights in the invention.---

Signed and Sealed this
Seventeenth Day of May, 2016

Michelle K. Lee
*Director of the United States Patent and Trademark Office*